United States Patent [19]

Godtfredsen

[11] Patent Number: 5,244,664
[45] Date of Patent: Sep. 14, 1993

[54] TOPICAL PREPARATION FOR TREATMENT OF ALOPECIA

[75] Inventor: Wagn O. Godtfredsen, Vaerlose, Denmark

[73] Assignee: Leo Pharmaceutical Products Ltd., Ballerup, Denmark

[21] Appl. No.: 817,816

[22] Filed: Jan. 8, 1992

Related U.S. Application Data

[63] Continuation-in-part of Ser. No. 543,763, Jul. 17, 1990, abandoned.

[30] Foreign Application Priority Data

Jan. 21, 1988 [GB] United Kingdom ............... 8801318

[51] Int. Cl.$^5$ ............................................. A61K 7/06
[52] U.S. Cl. ................................... 424/401; 424/70; 514/256; 514/255; 514/349
[58] Field of Search ................. 424/401, 70, 72; 514/256, 255, 349

[56] References Cited

U.S. PATENT DOCUMENTS

Re. 31,244  5/1983  Petersen ........................ 514/349
5,011,837   4/1991  Atwal et al. .................... 514/255

*Primary Examiner*—Thurman K. Page
*Attorney, Agent, or Firm*—Cushman, Darby & Cushman

[57] ABSTRACT

This invention relates to pharmaceutical compositions for treatment of alopecia comprising a compound of formula, in the form of the free base or acid addition salts thereof, in association with a pharmaceutical carrier adapted for topical application to mammalian skin. The compounds used have general formula

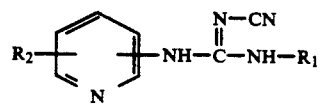

in which the $R_1$-substituted cyanoguanidyl radical is placed in the 3- or 4-position of the pyridine ring, and in which $R_1$ stands for a straight or branched, saturated or unsaturated, aliphatic hydrocarbon radical having from 1 to 8 carbon atoms, a cycloalkyl or cycloalkenyl radical having from 3 to 7 carbon atoms, or an aryl or an aralkyl radical. $R_2$ stands for hydrogen, halogen, hydroxy, lower alkyl or alkoxy radicals. The present compositions find applications both in the human and veterinary use.

10 Claims, No Drawings

TOPICAL PREPARATION FOR TREATMENT OF ALOPECIA

The present application is a continuation-in-part of Ser. No. 07/543,763, filed Jul. 17, 1990, abandoned.

This invention relates to pharmaceutical compositions for topical application comprising a compound of the formula I, in the form of the free base or acid addition salts thereof, in association with a pharmaceutical carrier adapted for topical application to mammalian skin.

Another aspect of the invention is a process for increasing the rate of terminal hair growth and a process for stimulating the conversion of vellus hair to growth as terminal hair.

The compounds used in the present composition and process are known as hypotensives, e.g. described in U.S. Pat. No. Re. 31,244. They have the general formula I:

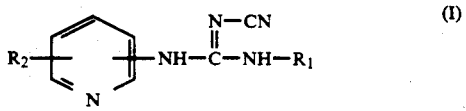

in which the $R_1$-substituted cyano-guanidyl radical is placed in the 3- or 4-position of the pyridine ring, and in which $R_1$ stands for a straight or branched, saturated or unsaturated, aliphatic hydrocarbon radical having from 1 to 8 carbon atoms, a cycloalkyl or cycloalkenyl radical having from 3 to 7 carbon atoms, or an aryl or an aralkyl radical. $R_2$ stands for hydrogen, halogen, hydroxy, lower alkyl or alkoxy radicals. The present invention comprises all stereoisomers of formula I as well as mixtures thereof.

In particular, the present composition and process use as active compound of formula I either N-tert-butyl-N''-cyano-N'-3-pyridylguanidine (in the following also designated P 1060, or N''-cyano-N-4-pyridyl-N'-1,2,2-trimethylpropylguanidine (in the following also designated pinacidil). As will be evident, the $R_1$ substituent in these compounds ins branched alkyl ($C_4$ or $C_6$). A representative $C_5$-branched alkyl is N-cyano-N-tertpentyl-N'-3-pyridinylguanidine which is designated herein as P1075.

Alopecia (a partial or complete loss of hair may result from genetic factors, aging, or from local or sysstemic disease. Male-pattern baldness is extremely common, it is familial and requires the presence of androgens, but other etiological factors are unknown. Female-pattern alopecia is not infrequent in women. It is ordinarily confined to thinning of hair in the frontal and the parietal regions. Complete baldness in any area is rare.

Alopecia is due to a deficiency of terminal hair which is the visual coloured hair. If the hair loss is due to atrophy or scarring, no regrowth can be expected. But in other cases, even where there is a noticeable absence of terminal hair, the skin of a seemingly bald person may contain the socalled vellus hair which is a very fine colourless hair, the presence of which needs microscopic determination. The vellus hair is a precursor to the terminal hair, and a regrowth may thus be promoted both by influencing the conversion of vellus hair to terminal hair and by stimulating the growth of the latter.

As alopecia is mainly a cosmetic problem, any therapy should never present risks which are unjustifiable. It has surprisingly turned out that the present compositions can be effectively used for the desired purpose. They find applications both in the human and veterinary use, the latter in particular being of economic importance in connection with animals raised for their pelts, e.g. mink. The present compositions can be used over the entire surface of the body for improving the pelt for commercial reasons, or they can be used partially to cure e.g. bald patches.

The pharmaceutical compositions contemplated by this invention include pharmaceutical compositions suited for topical application.

The term "topical" as employed herein relates to the use of a compound of the formula I, incorporated in a suitable pharmaceutical topical base in form of a solution and/or a suspension in which the active compound is suspended as a microfine powder. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, and the like. The term "ointment" embraces formulations (including creams) having oleaginous, absorption, water-soluble and emulsion-type bases, e.g. petrolatum, lanolin, polyethylene glycols, as well as mixtures of these.

The present compositions may advantageously further contain percutaneous penetration enhancers, such as N-methyl-2-pyrrolidone, azone, propylene glycol, and poly(oxyethylene)-poly(oxypropylene) co-polymers.

The percentage by weight of the compound of the formula I herein utilized ranges from about 0.1% to about 20.0% of the pharmaceutical preparation, preferably from about 0.5% to about 5% and in these preparations the aforesaid pharmaceutical carrier for topical application constitutes a major amount of the said preparation.

The following examples describe the manner and process of making and using the invention and set forth the best mode contemplated by the inventor of carrying out the invention but are not to be construed as limiting.

EXAMPLE 1

| Topical ointment | |
|---|---|
| P 1060 | 20 g |
| Paraffin, liquid | 200 g |
| White soft paraffin to make | 1000 g |

The fatty ingredients are melted at increased temperature, and the active substance P 1060 is incorporated by homogenizing. The ointment is cooled and filled into suitable containers.

EXAMPLE 2

| Topical ointment | |
|---|---|
| Pinacidil | 100 g |
| Sorbitan sesquioleate | 50 g |
| Paraffin, liquid | 100 g |
| White soft paraffin to make | 1000 g |

Preparation as described in Example 1.

EXAMPLE 3

| Topical (waterfree/watermiscible) ointment | |
| --- | --- |
| P 1060 | 50 g |
| Polyethylene glycol 400 | 250 g |
| Polyethylene glycol 4000 | 700 g |

The glycols are melted at increased temperature. The active substance P 1060 is incorporated. The preparation is cooled and filled into suitable containers.

EXAMPLE 4

| Topical cream | |
| --- | --- |
| Pinacidil | 50 g |
| Paraffin, liquid | 100 g |
| White soft paraffin | 50 g |
| Cetyl alcohol | 100 g |
| Polyoxyethylene sorbitan monostearate | 50 g |
| Methylparaben | 2 g |
| Propylparaben | 0.2 g |
| Glycerol | 100 g |
| Water to make | 1000 g |

The fatty ingredients including the emulsifying agent are melted by increased temperature. At increased temperature the water phase including the active substance pinacidil and a solution of the preservative are mixed with the melted fatty phase. The cream is homogenized, cooled, and filled into suitable containers.

EXAMPLE 5

| Topical cream | |
| --- | --- |
| P 1060 | 10 g |
| Cetostearyl alcohol | 100 g |
| White soft paraffin | 150 g |
| Liquid paraffin | 50 g |
| Cetomacrogal 1000 | 20 g |
| Chlorocresol | 1 g |
| Water to make | 1000 g |

Preparation as described in Example 4.

EXAMPLE 6

| Topical hydrogel | |
| --- | --- |
| Pinacidil | 50 g |
| Carbomer | 10 g |
| Methylparaben | 2 g |
| Propylparaben | 0.2 g |
| Silicone oil | 30 g |
| Triethanolamine | 5 g |
| Water to make | 1000 g |

The preservatives are dissolved and mixed with the carbomer. A gel is formed by the addition of triethanolamine. Finally, pinacidil and silicone oil are added, and the gel is homogenized.
The gel is filled into suitable containers.

EXAMPLE 7

| Topical gel | |
| --- | --- |
| P 1060 | 10 g |
| Liquid paraffin | 20 g |
| Cetostearyl alcohol | 20 g |
| Polyoxyethylene-2-stearylether | 3 g |
| Polyoxyethylene-10-stearylether | 7 g |
| Methylparaben | 2 g |
| Propylparaben | 0.2 g |
| Propylene glycol | 100 g |
| Carbomer | 10 g |
| Triethanolamine | 5 g |
| Water to make | 1000 g |

The fatty ingredients including the emulsifying agent are melted at increased temperature. The water phase including a solution and/or a homogeneous suspension of the active substance P 1060, the preservatives, and the carbomer are mixed with the fatty phase.

The mixture is homogenized, gelled by the addition of the triethanolamine, and then filled into suitable containers.

EXAMPLE 8

| Topical lotion | |
| --- | --- |
| P 1060 | 30 g |
| Propylene glycol | 50 g |
| Isopropyl alcohol | 850 g |
| Water to make | 1000 g |

The active substance is dissolved in the pharmaceutical base.

EXAMPLE 9

| Topical lotion | |
| --- | --- |
| Pinacidil | 50 g |
| Polyethylene glycol 4000 | 120 g |
| Myristyl-γ-picolinium chloride | 0.2 g |
| Polyvinylpyrrolidone | 1 g |
| Deionized water q.s. ad | 1000 c.c. |

The ingredients are dissolved in water and filled into containers.

The composition so prepared can be used in the topical treatment of baldness by application to the scalp daily.

EXAMPLE 10

| Topical spray Aerosol (foam) | |
| --- | --- |
| P 1060 | 10 g |
| Polawax A 31 | 40 g |
| Ethyl alcohol | 600 g |
| Polyvinylpyrrolidone | 30 g |
| Glycerol | 10 g |
| Water | 220 g |
| Dichlorodifluoromethan | 40 g |
| Dichlorotetrafluoroethan | 60 g |

All ingredients are dissolved or suspended in ethyl alcohol and the water. The concentrate is filled into aerosol containers and the propellants are added.

EXAMPLE 11

| Topical Spray Aerosol | |
| --- | --- |
| Pinacidil | 1.5 g |

-continued

| Topical Spray Aerosol | |
|---|---|
| Absolute alcohol | 4.3 g |
| Dichlorodifluoroethane | 1.43 g |
| Dichlorotetrafluoroethane | 5.70 g |

The pinacidil is suspended in the absolute alcohol. The suspension is chilled to about minus 30° C. To this is added the chilled mixture of dichlorodifluoromethane and dichlorotetrafluoroethane. 13 ml plastic-coated amber bottles are cold filled with 11.5 g each of the resulting solution and capped.

The compositions can be sprayed on the scalp daily to convert vellus hair to growth as terminal hair.

EXAMPLE 12

| Dusting Powder | |
|---|---|
| P 1060 | 10 g |
| Magnesium stearate | 5 g |
| Silicone dioxide colloidal | 10 g |
| Lactose | 478 g |
| Maize starch | 500 g |

The powdered ingredients are mixed together.

EXAMPLE 13

| Dusting Powder | |
|---|---|
| P 1060 | 10 g |
| Bentonite | 100 g |
| Talc q.s. | 1000 g |

The powdered ingredients are mixed together and dusted on the fur of minks for increasing the rate of hair growth.

EXAMPLE 14

Topical lotion containing N''-cyano-N-(tert-pentyl)-N'-3-pyridinylguanidine (P 1075)

| P 1075 | 10 g |
|---|---|
| Propylene glycol | 500 g |
| Ethyl alcohol | 500 g |

P 1075 dissolved in the mixture of propylene glycol and ethyl alcohol at room temperature. The resulting composition is used in the same way as the other exemplified formulations.

EXAMPLE 15

Topical lotion containing N''-cyano-N-(tert-pentyl)-N'-3-pyridinylguanidine (P 1075)

| P 1075 | 5 g |
|---|---|
| Propylene glycol | 100 g |
| Isopropyl alcohol | 800 g |
| Water to make | 1000 g |

P 1075 is dissolved in isopropyl alcohol and propylene glycol and water are added. This composition can be used to increase the rate of hair growth.

What we claim is:

1. A process for increasing the rate of terminal hair growth in mammalian species comprising the application to mammalian skin at the locale of terminal hair of an effective amount of a compound of formula I:

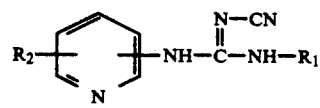

in which the $R_1$- substituted cyano-guanidyl radical is placed in the 3- or 4-position of the pyridine ring, and in which $R_1$ stands for a straight or branched, saturated or unsaturated, aliphatic hydrocarbon radical having from 1 to 8 carbon atoms, a cycloalkyl or cycloalkenyl radical having from 3 to 7 carbon atoms, or an aryl or an aralkyl radical, and $R_2$ stands for hydrogen, halogen, hydroxy, lower alkyl or alkoxy radicals; all stereoisomers thereof and mixtures of same, and the pharmaceutically acceptable acid addition salts thereof; in association with a topical pharmaceutical carrier.

2. The process of claim 1 wherein the concentration of the compound applied is from about 0.1% to about 20% of the composition.

3. The process of claim 1, wherein compound applied is N-tert-butyl-N''-cyano-N'-3-pyridylguanidine.

4. The process of claim 1 wherein compound applied is N''-cyano-N-4-pyridyl-N'-1,2,2-trimethylpropylguanidine.

5. A process for the conversion of vellus hair to growth as terminal hair comprising the application to mammalian skin at the locale of vellous hair of an effective amount of a compound of formula I:

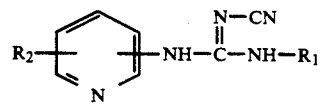

in which the $R_1$-substituted cyano-guanidyl radical is placed in the 3- or 4-position of the pyridine ring, and in which $R_1$ stands for a straight or branched, saturated or unsaturated, aliphatic hydrocarbon radical having from 1 to 8 carbon atoms, a cycloalkyl or cycloalkenyl radical having from 3 to 7 carbon atoms, or an aryl or an aralkyl radical, and $R_2$ stands for hydrogen, halogen, hydroxy, lower alkyl or alkoxy radicals; all stereoisomers thereof and mixtures of same, and the pharmaceutically acceptable acid addition salts thereof; in association with a topical pharmaceutical carrier.

6. The process of claim 5 wherein the concentration of the compound applied is from about 0.1% to about 20% of the composition.

7. The process of claim 5 wherein the compound applied is N-tert-butyl-N''-cyano-N'-3-pyridylguanidine.

8. The process of claim 5 wherein the compound applied is N''-cyano-N-4-pyridyl-N'-1,2,2-trimethylpropylguanidine.

9. A process as claimed in claim 5 wherein $R_1$ is alkyl of 1-8 carbons and $R_2$ is hydrogen.

10. A process as claimed in claim 9 wherein $R_1$ is branched alkyl of 4 to 6 carbons.

* * * * *